United States Patent [19]

Morkun et al.

[11] Patent Number: 5,058,432

[45] Date of Patent: Oct. 22, 1991

[54] METHOD AND APPARATUS FOR MEASURING PARAMETERS OF SOLID PHASE OF SLURRIES

[76] Inventors: Vladimir S. Morkun, prospekt Karla Marxa, 43, kv. 6; Valentin P. Khorolsky, ulitsa Pushkina, II, kv. 32, both of Krivoi Rog; Vladimir S. Protsuto, ulitsa Nalichnaya, 36, kv. 90, Leningrad; Viktor N. Potapov, ulitsa Bljukhera, 5, kv. 57, Krivoi Rog, all of U.S.S.R.

[21] Appl. No.: 324,173

[22] Filed: Mar. 16, 1989

Related U.S. Application Data

[63] Continuation of Ser. No. 130,535, Sep. 23, 1987, abandoned.

[51] Int. Cl.$^5$ ............................................. G01N 9/24
[52] U.S. Cl. ..................................... 73/599; 73/61 R
[58] Field of Search ..................... 73/599, 61 R, 32 A, 73/865.5, 597, 602, 592

[56] References Cited

U.S. PATENT DOCUMENTS

| 4,381,674 | 3/1983 | Abts ........................................ | 73/599 |
| 4,412,451 | 11/1983 | Uusitalo et al. ........................ | 73/599 |
| 4,667,515 | 5/1987 | Farren et al. .......................... | 73/61 R |
| 4,739,662 | 4/1988 | Foote ..................................... | 73/599 |

FOREIGN PATENT DOCUMENTS

| 785755 | 12/1980 | U.S.S.R. |  |
| 896542 | 1/1982 | U.S.S.R. |  |
| 0901894 | 1/1982 | U.S.S.R. | 73/599 |
| 953546 | 8/1982 | U.S.S.R. |  |

OTHER PUBLICATIONS

Khan J. A., "Oprobovanie i Kontrol. . . Obogascheniya" M, Nedra, 1979, pp. 119-120-without translation.

"Analizette 20", Prospect firmy Fritsch, D-6580, IDAR-Obershtain-I (GFR)-without translation (no date).

Reklamu firmy Armco Grinding Systems, "Take Control of Your Grinding Circuit" (undated).

Primary Examiner—Hezron E. Williams
Assistant Examiner—Louis M. Arana
Attorney, Agent, or Firm—Lilling and Lilling

[57] ABSTRACT

A method for measuring parameters of solid phase of slurries having the following steps: forming ultrasonic oscillations and emitting them into a fluid under study, forming the Lamb waves and directing them into a wall of a vessel containing the fluid under study, forming acoustic currents and radiation pressure of sonic radiation in the fluid under study, and measuring amplitude and length of pulses of ultrasonic oscillations that pass through the fluid under study and the Lamb waves that pass through a predetermined distance along the wall of the vessel containing the fluid under study without and with the action of the acoustic currents and radiation pressure of sonic radiation, the values of which are used for the assessment of concentration of solid phase of the fluid under study. An apparatus for carrying out the method has two measurement channels each having a logarithmic converter, a subtraction unit and a division unit.

23 Claims, 5 Drawing Sheets

METHOD AND APPARATUS FOR MEASURING PARAMETERS OF SOLID PHASE OF SLURRIES

This is a continuation of application Ser. No. 07/130,535, filed on Sept. 23, 1987, now abandoned.

BACKGROUND OF THE INVENTION

1. Field of the Invention

The invention relates to equipment for measuring parameters of production processes, and more particularly, it deals with methods for measuring parameters of the solid phase of slurries and an apparatus for carrying out the method.

2. Description of the Prior Art

Known in the art are various methods for measuring parameters of the solid phase of slurries.

Thus a method and apparatus are widely used for measuring particle size of the solid phase in slurries (cf. Kn. Khan J.A. "Oprobovanie i kontrol teknnologicheskikh processov obogascheniya", M., "Nedra", 1979, pp. 119-120) which are based on determining the position of a micrometric feeler, which reciprocates in the flow of the slurry under study, at the moment it is stopped owing to a solid phase particle being retained between the surfaces of the micrometric feeler and a trough along which the slurry is supplied.

The prior art method and apparatus are deficient due to rapid wear, hence, low reliability of the micrometric feeler which is permanently in contact with abrasive particles of the slurry under study. This results in a scatter of results in measuring the solid phase particles in slurries having the same particle size, i.e. in a low accuracy of measurements.

Also known in the art are a method and apparatus for measuring particle size of the solid phase of slurries (cf., for example, razvertyvauschii fotosediment graf "Analizette 20", prospect firmy FRITSCH". D-6580, IDAR-Obershtain -I (GFR) based on the measurement of the time of setting of solid phase particles of a slurry in a vessel containing water.

However, the abovementioned method requires preliminary sampling of the slurry under study from the production flow, extraction of the solid phase from the slurry sample, weighing and delivery to the place of measurement. This results in long measurement times (about 20 to 40 minutes) thus greatly restricting the field of application.

Known in the art is a method for measuring parameters of solid phase of slurries (cf., for example Armco Grinding Systems, "Take Control of four Grinding Circuil) based on directing radiation into the fluid under study. Ultrasonic; oscillations at two fixed frequencies are used,, measuring the amplitude of ultrasonic oscillations that pass through the fluid under study and assessing the concentration of the solid phase and the concentration of the critical particle size fraction of the solid phase in the slurry under study by the value of this amplitude, the slurry under study being degassed before directing ultrasonic oscillations thereinto in a special tank by combined action of vacuum and centrifugal forces generated by an impeller.

Known in the art is an apparatus for carrying out the method for measuring parameters of the solid phase of slurries (cf., for example, ibid.,) comprising two measurement channels, each consisting of a series circuit including a pulse generator, a power amplifier an emitting ultrasonic transducer, a receiving ultrasonic transducer, a received pulse amplifier, and an electronic switch. The apparatus also comprises a one-shot multivibrator connected between the pulse generator and electronic switch and also a switching circuit connected between the pulse generators of the two channels, a multivibrator having an output connected to the input of the switching circuit, a comparator, a setting means, a study function selector, a recorder, and also a mechanical gas bubble separator consisting of a tank for air removal and an impeller having a drive motor. The emitting and receiving transducers of one of the measurement channels are secured directly to the walls of a vessel containing a fluid under study.

It should be noted, however, that since it is necessary in the abovedescribed method and apparatus to effect the preliminary removal of gaseous phase from the fluid under study, hence, to have a mechanical gas bubble separator in the form of an apparatus including a rotary impeller, reliability of the process of measurement of parameters of the solid phase in slurries is rather low.

Under the action of abrasive particles in the slurry under study, intensive wear of rotating parts of the mechanical gas bubble separator occurs which results in variations of its characteristics, hence, in changes in quality of degassing during operation. To maintain quality of degassing at the desired level, regular stoppage of the apparatus for measuring parameters of the solid phase of slurries is necessary for maintenance and replacement of worn mechanical components. The drive motor of the impeller consumes much energy which results in added cost bearing in mind continuous operation of the measuring apparatus. Therefore, the use of the mechanical gas bubble separator lowers reliability, impairs accuracy of measurements and results in an increased cost of both the apparatus for measurement as a whole and operation.

SUMMARY OF THE INVENTION

It is an object of the invention to provide a method and apparatus for measuring parameters of the solid phase of slurries which make it possible to improve accuracy and reliability of measurements of the concentration of the solid phase and concentration of a critical particle size fraction of the solid phase in the slurry under study.

This is accomplished by a method for measuring parameters of the solid phase of slurries, comprising forming pulses of ultrasonic oscillations, causing them to pass through a fluid under study containing a slurry, measuring the amplitude of ultrasonic oscillations that passed through the fluid. According to the invention, the method also comprises forming Lamb waves and causing them to pass along the wall of a vessel containing the fluid under study, measuring the amplitude of the Lamb waves that passed through a predetermined distance along the wall of the vessel containing the fluid under study, the amplitude characterizing concentration of the solid phase of the slurry, computing the ratio of the differences between logarithms of the measured amplitudes of the ultrasonic oscillations that pass through the fluid under study and of the Lamb waves that pass through the predetermined distance along the wall of the vessel containing the fluid under study to a logarithm of the measured amplitude of Lamb waves, the ratio corresponding to the concentration of a critical particle size fraction of the solid phase of the slurry, forming in the fluid under study acoustic currents and a radiation pressure of a sonic radiation, the intensity of which is proportional to the mass of particles of the solid phase of the slurry, determining the quotient of division of the computed ratios for several fixed values of intensities of acoustic currents and radiation pressure of a sonic radiation to the same value obtained without these factors, which characterizes the concentration of a useful component in critical particle size fractions of the slurry under study.

The above features allow concentration of the solid phase and concentration of a useful component in critical size fractions of the fluid under study to be measured without preliminarily removing gaseous phase from the fluid thus simplifying the measurement process, improving reliability and accuracy of measurement results.

It is preferred that two levels of measurement of the pulse length of ultrasonic oscillations that pass through the fluid under study and Lamb waves that pass through a predetermined distance along the wall of a vessel containing the fluid under study be formed by successively limiting their amplitude, the levels of measurement of the length of these pulses being varied proportionally with their amplitude, the length of the received pulses at the levels thus formed being measured, the difference between the measured values for the Lamb waves that pass through the predetermined distance along the wall of the vessel containing the fluid under study being computed to characterize the concentration of the solid phase of the slurry, and the ratio of the difference between the measured values for ultrasonic oscillations that pass through the fluid under study to the difference of the measured values for the Lamb waves that pass through the predetermined distance along the wall of the vessel containing the fluid under study without the action of acoustic currents and radiation pressure being computed to represent the concentration of the critical particle size fraction of the solid phase of the slurry.

This facility makes it possible to improve accuracy of measurement of the concentration of the solid phase, concentration of the critical particle size fraction of the solid phase and concentration of a useful component in the critical fractions of the fluid under study in applications where the concentration of gaseous phase has a volume which is larger than that of the solid phase.

The object is also accomplished by an apparatus for measuring parameters of the solid phase of a slurry, comprising two measurement channels, each having a series circuit including a pulse generator and an emitting ultrasonic transducer and a series circuit including a receiving ultrasonic transducer and a received signal amplifier, the emitting and receiving ultrasonic transducers of one measurement channel being secured directly to the walls of a vessel containing a fluid under study. According to the invention, the apparatus also comprises, in each measurement channel, a logarithmic converter connected to the output of the received signal amplifier, a subtraction unit having inputs to which are connected the outputs of the logarithmic converters of the both channels, and a division unit having inputs to which are connected the output of the subtraction unit and the output of the logarithmic converter of the second measurement channel, the ultrasonic emitting and receiving transducers of the second measurement channel being mounted on forming prisms secured to the wall of the vessel containing the fluid under study.

The forming prisms may be mounted on a plate covering longitudinally extending apertures in the wall of the vessel containing the fluid under study, the plate being secured to the vessel wall.

This construction allows a mechanical gas bubble separator to be dispensed with in operation of the apparatus for measuring parameters of the solid phase of a slurry thus improving accuracy and reliability of the apparatus as a whole and also lowering the cost of its manufacture and operation. The apparatus allows the concentration of the solid phase to be measured concurrently with the concentration of a critical particle size fraction of the solid phase of the fluid being studied.

Each measurement channel may comprise a pulse expander, the input of each expander being connected to the output of the received pulse amplifier and the outputs, to the inputs of the subtraction unit, the output of the pulse expander of the second measurement channel being also connected to the input of the division unit.

The apparatus preferably comprises a counter having its input connected to the output of the received signal amplifier, an OR gate having its output connected, via its own delay line, to the inputs of the pulse generators, a decoder having its inputs connected to the output of the counter and an output connected to the input of the OR gate, and a control system for controlling the process of measurement and computation of parameters of the solid phase of slurries cooperating with the decoder and OR gate.

This arrangement makes it possible to conduct measurements of the concentration of the solid phase, concentration of a critical particle size fraction of the solid phase and concentration of a useful component in critical fractions of the slurry under study without preliminarily removing gaseous phase.

It is preferred that the control system for controlling the process of measurement and computation of parameters of the solid phase of a slurry under study comprises a series circuit including a second OR ate, a third pulse generator and a third emitting transducer secured to the wall of the vessel above the two former transducers mounted on forming prisms and opposite thereto, the inputs of the second OR gate being connected, via its own one-shot multivibrator, to the inputs of the first OR gate and to the outputs of the decoder.

The control system for controlling the measurement process and for computing parameters of solid phase of a slurry under study preferably comprises at least four identical series circuits each including: a delay line, an electronic switch, an amplitude detector and a second electronic switch, as a second division unit having inputs to which are connected the outputs of all these series circuits, the output of this division unit being the data output of the whole apparatus; the outputs of at least three of said series circuits being put together to form a common output, the inputs said delay lines of all said series circuits being connected to the inputs of said decoder; the data input of said first electronic switch of each said series circuit being connected to the output of said first division unit; the control input of said second electronic switch of said first series circuit being connected, via a series circuit including an OR gate and one-shot multivibrator, to the fifth, sixth and seventh outputs of said decoder, the control input of said second electronic switch of said other series circuits having their outputs put together being connected to the output of said decoder via a respective one-shot multivibrator, and the control input of said amplitude detector in each of said series circuits being connected to the output of said decoder.

In each measurement channel, the output of the logarithmic converter is preferably connected to a series circuit including a delay line, an amplitude limiter, a control circuit and a unit for computing the difference between pulse lengths at different limitation levels, the output of each being connected to the input of the subtraction unit.

The apparatus may comprise two identical circuits for forming limitation level each comprising a unit for selecting the limitation level having its input connected to the output of a respective logarithmic converter and the output connected to the control input of a respective amplitude limiter, and a series circuit including a second amplitude limiter and a clock control circuit connected to a respective amplitude limiter, the clock having its output connected to the input of a respective unit for computing pulse length difference.

In each measurement channel, the output of the logarithmic converter may be connected to a second unit for selecting limitation level having its output connected to the control input of a respective second amplitude limiter.

The abovedescribed facilities make it possible to improve accuracy of measurement of parameters of solid phase in slurries in applications where concentration of the gaseous phase is of a volume greater than that of the solid phase, without preliminary removal of the gaseous phase.

BRIEF DESCRIPTION OF THE DRAWINGS

The invention will now be described in details with reference to specific embodiments shown in the accompanying drawings, in which.

DESCRIPTION OF THE PREFERRED EMBODIMENTS

A method for measuring parameters of solid phase of slurries according to the invention comprises the following steps.

Figure 1:
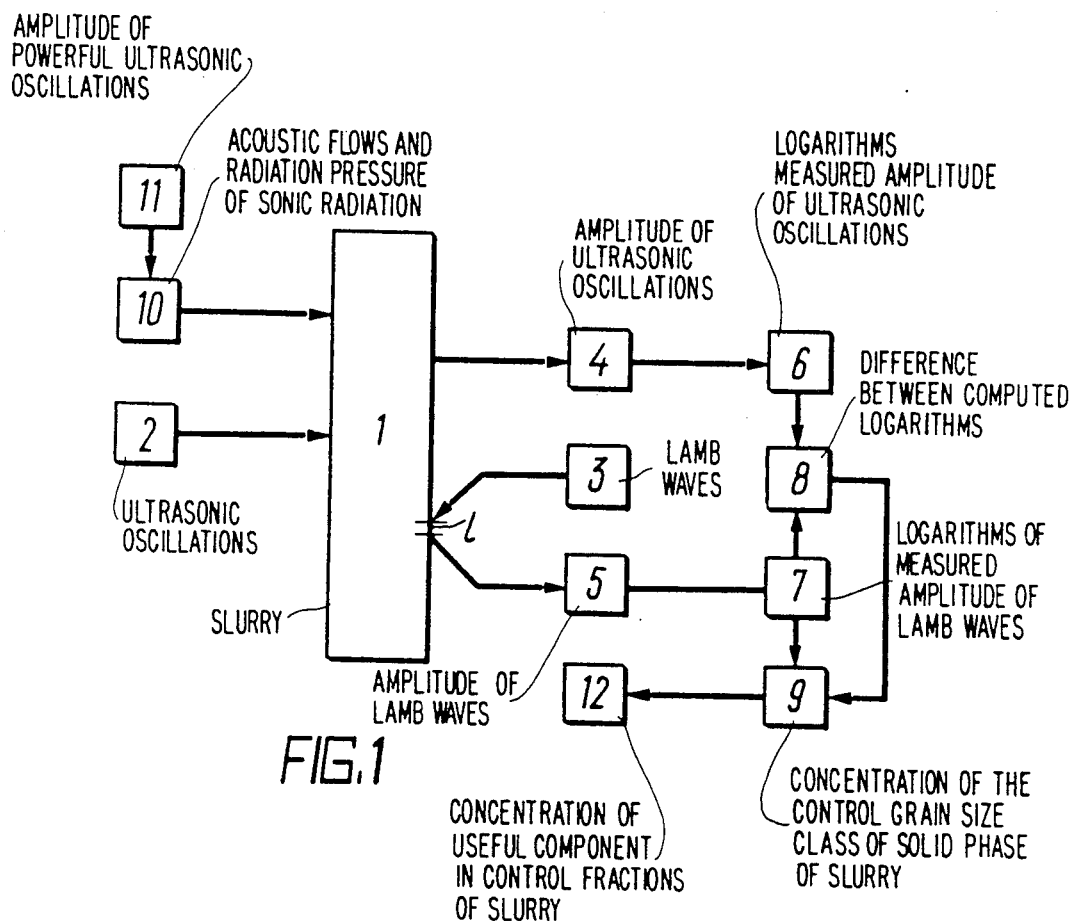
FIG. 1 schematically shows steps of a method for measuring parameters of solid phase of slurries according to the invention.

Ultrasonic oscillations 2 are formed and caused to pass through a fluid or slurry under study (FIG. 1), the wavelength of the oscillations being commensurate with the particle size of solid phase of the slurry 1 being studied. When the ultrasonic oscillations 2 propagate through the slurry 1, their energy is absorbed and scattered. Scattering of the ultrasonic oscillations prevail over absorption in case the particle size is commensurate with the oscillations wavelength. Generally speaking, the amount of damping of ultrasonic oscillations 2 at a fixed frequency in the slurry 1 under study depends on concentration and particle size of the solid phase. It should be noted that the ratio between absorption and scattering of the ultrasonic oscillations 2 depends on the fraction of particles of solid phase whose size is commensurate with the wavelength of the oscillations 2 being used.

Gas bubbles are the disturbing factor in measuring the value of attenuation of ultrasonic oscillations 2 in the slurry 1 being studied. The process of damping of the ultrasonic oscillations 2 at gas bubbles is of a manifest resonance nature.

With an increase in frequency of the ultrasonic oscillations 2 the amount of resonance-size bubbles in the slurry 1 being studied substantially decreases, and this amount is practically reduced to zero at frequencies of 5 MHz and higher. This is due to the fact that the resonance frequency of gas bubbles increases with a decrease in their size, and when the gas bubble is diminished to a predetermined limit, it is dissolved in water.

Therefore, the amount of damping of the ultrasonic oscillations 2 at high frequency, when they are caused to pass through the fluid 1 under study, substantially depends only on solid particle size and solid phase concentration, gas bubbles of non-resonance size influencing this amount only with a very high concentration of gaseous phase.

Lamb waves 3 are concurrently formed and caused to pass along the wall of a vessel containing the fluid 1 under study. The amount of damping of Lamb waves 3 in the vessel wall only depends on the distance they pass through and the concentration of solid phase of the fluid 1 being studied. This amount does not depend on solid phase particle size and concentration of gas bubbles (because of their small mass).

After the ultrasonic oscillations 2 have passed through the fluid 1 under study and the Lamb waves 3 have passed through a predetermined distance 1 along the wall of a vessel containing the fluid 1 under study, their amplitudes 4, 5 are measured. Logarithms 6, 7 of the measured amplitudes 4, 5 are computed, and a difference 8 is computed between the computed logarithms.

A value S (ref. numeral "9" in FIG. 1) equal to $$S = \frac{S_2 - S_1}{S_1},$$

wherein $S_1$ is the logarithm of the amplitude of the Lamb waves 3 that pass through a predetermined distance 1 along the wall of a vessel containing the fluid 1 under study;

$S_2$ is the logarithm of the amplitude of the ultrasonic oscillations 2 that pass through the medium 1 under study, which characterizes the concentration of the particle size fraction of solid phase of the slurry 1 under study, i.e. the concentration ω±r of particles of a comminuted material having a size which is larger or smaller than a pre-set critical size.

The amount of displacement of particles of a known size from the state of equilibrium or from steady path of their movement under the action of external factors in a slurry having a known concentration ω depends on their specific gravity. In case the specific gravity of a useful component of the fluid 1 under study is known the amount of deviation of particles of the useful component can be determined, and the amount of displacements of other particles of known size from the state of equilibrium or a steady path of their movement will characterize concentration of the useful component in critical particle size fractions of the slurry 1 under study.

For measuring this amount, acoustic or ultrasonic waves 10 are formed in the fluid 1 under study under the action of powerful ultrasonic oscillations. The intensity of the acoustic or ultrasonic waves 10 is controlled by varying amplitude 11 of powerful ultrasonic oscillations. Thus, they can act upon various fractions of the fluid 1 under study. Then a ratio 12 of the value S for the fluid under study without any action of powerful ultrasonic oscillations (designated $S_o$) to the same value S with the action of acoustic currents and radiation pressure of the sonic radiation 10 of a known intensity is computed to characterize a concentration of the useful component in critical particle size fractions of the slurry under study.

If concentration of the gaseous phase has a volume commensurate with concentration of the solid phase which is but very rare in practical applications, it is preferable to carry out a double treatment of the fluid 1 under study with acoustic currents and radiation pressure of the sonic radiation 10 to improve accuracy of measurement of parameters of solid phase of slurries. At the first stage, this is made before the fluid 1 under study has been admitted to the zone where parameters of solid phase are measured so as to contribute to a removal of the gaseous phase into the atmosphere, and at the second stage, the same step is used for measuring concentration of the useful component in critical particle size fractions of the fluid under study as described above.

Accuracy of measurement of concentration of solid phase and concentration of critical particle size fractions of solid phase of slurries with a high content of gaseous phase may also be improved in another manner.

For that purpose, a change in the form of pulses of the ultrasonic oscillations 2 that pass through the fluid 1 under study and of the Lamb waves 3 that pass through a predetermined distance I along the wall of a vessel containing the fluid under study is analyzed.

Under the action of inertia properties of the slurry 1 under study, the original form of a pulse is distorted. In case the emitted pulse is square, the distortion manifests itself in a gradual rise of the leading and decrease in the trailing edge. Inertia properties of actual slurries depend substantially on their concentration and grading of solid phase of slurries since the mass of particles of a comminuted material is several orders greater than the mass of gas bubbles.

Particles of a comminuted material move together with liquid in the ultrasonic field. The character of this movement depends on frequency of ultrasonic oscillations and particle size: with an increase in particle size, with a fixed ultrasonic oscillations frequency, or with an increase in frequency, with a fixed particle size of a comminuted material the particles will lag behind the moving liquid more and more. The difference between inertia properties of a fluid under study manifests itself in the form of a change in the form of pulses of the ultrasonic oscillations 2 that pass through the fluid 1 under study and of the Lamb waves 3 that pass through a predetermined distance along the wall of a vessel containing the fluid 1 under study and depends on oscillations frequency, concentration and grading of solid phase of slurries.

Figure 2:
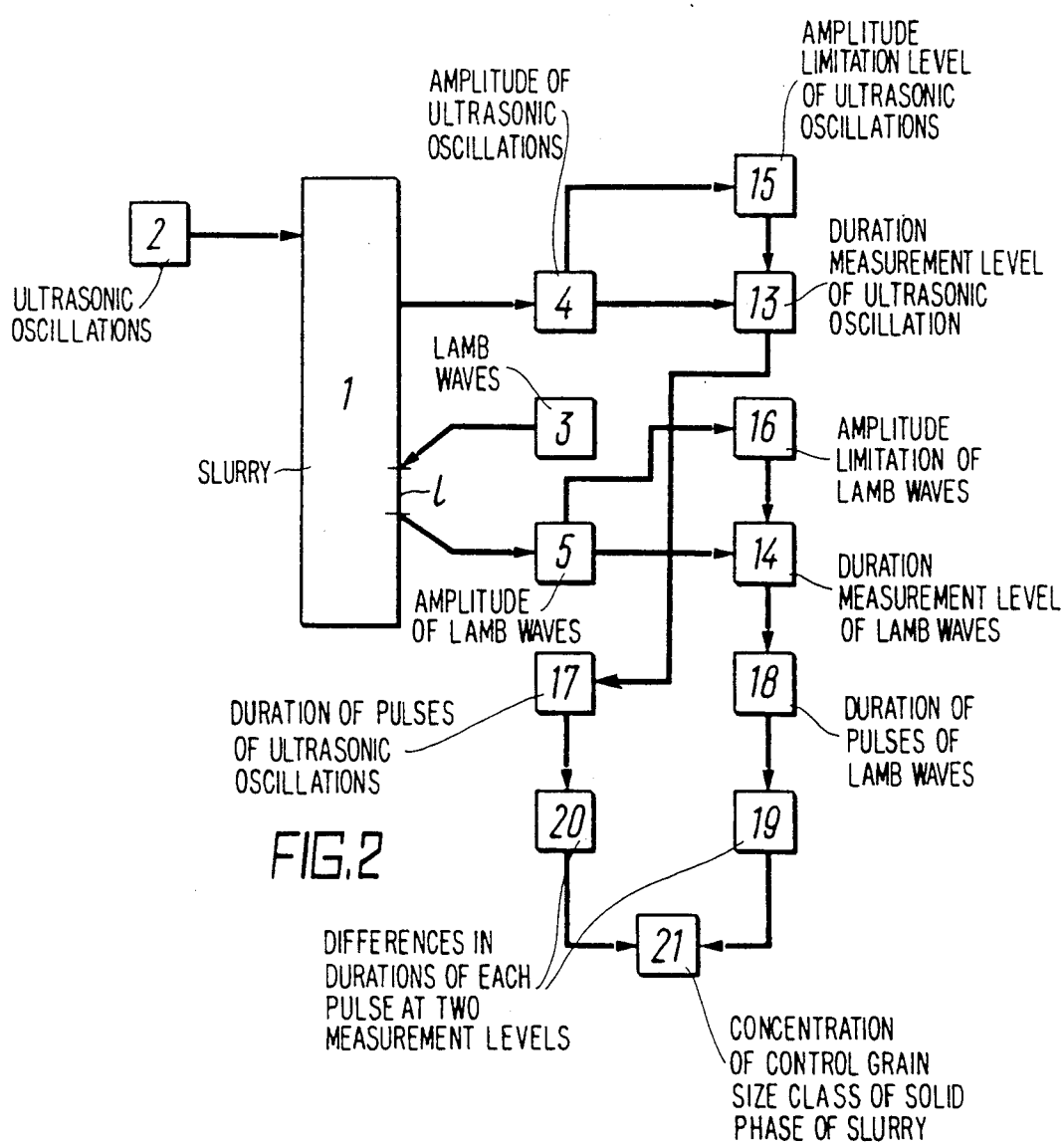
FIG. 2 schematically shows steps of a method for measuring parameters of solid phase of slurries with the control of the length of received pulses of ultrasonic oscillations that passed through the fluid under study and Lamb waves that passed through a predetermined distance along the wall of a vessel containing the fluid under study, according to the invention.

After the amplitudes 4, 5 of pulses of the ultrasonic oscillations 2 and Lamb waves 3 have been measured, two levels 13, 14 (FIG. 2) are formed at which to measure their lengths.

For that purpose, the received pulses are successively limited by amplitude. Limitation levels 15, 16 are chosen in such a manner that the ratio of the measured amplitude 4, 5 of the received pulses to the absolute value of amplitudes of this value be a constant value.

After the measurement of lengths 17, 18 of the ultrasonic oscillations pulses 2 that pass through the fluid 1 under study and Lamb waves 3 that pass through a predetermined distance I along the wall of a vessel containing the fluid 1 under study at the two levels 13, 14, differences 19, 20 between lengths of each pulse at the two levels 13, 14 are computed.

The difference 20 between pulse lengths of the Lamb waves that passed through a predetermined distance 1 along the wall of a vessel containing the fluid 1 under study will characterize concentration of solid phase of slurries.

A ratio 21 of the difference 19 between the lengths 17, 18 of pulses of the ultrasonic oscillations 2 that pass through the fluid 1 under study to the difference 20 between pulse lengths of the Lamb waves 3 that passed through a predetermined distance I along the wall of a vessel containing the fluid 1 under study represents concentration of a critical particle size fraction of slurries.

Figure 3:
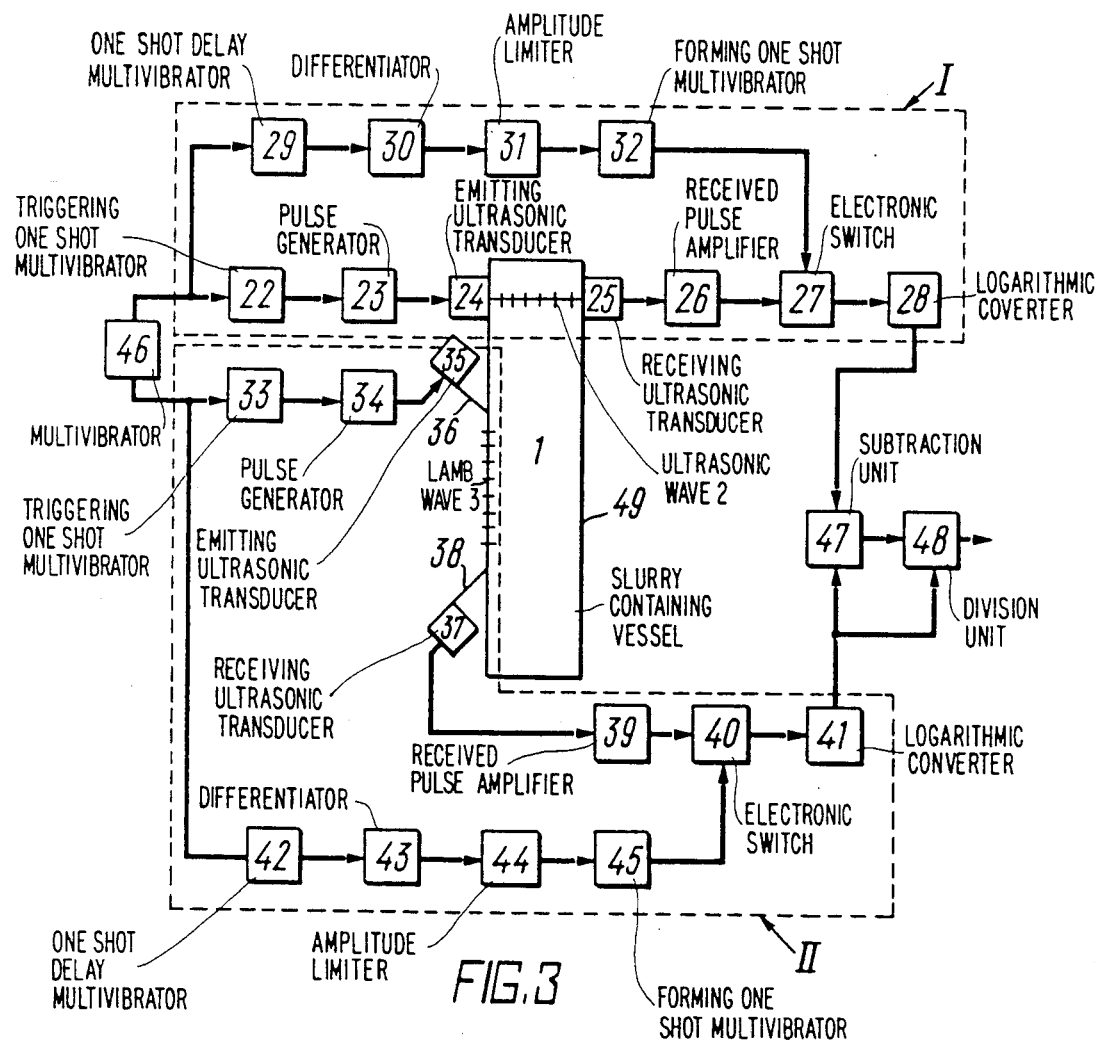
FIG. 3 shows a clock-diagram of an apparatus for carrying out the method for measuring parameters of solid phase of slurries which is designed for measuring concentration of solid phase and concentration of a critical particle size fraction of solid phase of slurries according to the invention.

An apparatus for carrying out the method for measuring parameters of solid phase and concentration of critical particle size of solid phase of slurries comprises two measurement channels I and II (FIG. 3).

The first measurement channel I consists of a series circuit including a triggering one-shot multivibrator 22, a pulse generator 23, an emitting ultrasonic transducer 24, a receiving ultrasonic transducer 25, a received pulse amplifier 26, and electronic switch 27 and a logarithmic converter 28. A series circuit connected to the input of the triggering one-shot multi vibrator 22 includes one-shot delay multivibrator 29, a differentiator 30, an amplitude limiter 31 and a forming one-shot multivibrator 32 having its output connected to the second input of the electronic switch 27.

The second measurement channel II consists of a series circuit including a triggering one-shot multivibrator 33, a pulse generator 34, an emitting ultrasonic transducer 35 mounted on a first forming prism 36, a receiving ultrasonic transducer 37 mounted on a second forming prism 38,, a received pulse amplifier 39, an electronic switch 40 and a logarithmic converter 41.

To the input of the triggering one-shot multivibrator 33 is connected a series circuit including a one-shot delay multivibrator 43, an amplitude limiter 44 and a forming one-shot multivibrator 45 having its output connected to the second input of the electronic switch 40.

A multivibrator 46 is connected to the inputs of the triggering one-shot multivibrators 22, 33. A subtraction unit 47 is connected between the logarithmic converters 28, 41 of both measurement channels I, II, the output of the subtraction unit being connected to one input of a division unit 48 having a second input to which is connected the output of the logarithmic converter 41 of the second measurement channel II.

The emitting 24 and receiving 25 ultrasonic transducers of the first measurement channel I as well as the forming prisms 36, 38 of the second measurement channel II are mounted on a vessel 49 containing the fluid 1 under study.

The multivibrator 46 generates pulses, each pulse triggering, via the triggering one-shot multivibrators 22, 33, the pulse generators 23, 34 forming square pulses filled with electric oscillations at a predetermined frequency. The time during which the pulse generators 23, 34 remain switched on, hence the length of square pulses formed thereby, will depend on the length of pulses formed by the triggering one-shot multivibrators 22, 33.

The emitting transducers 24, 35, e.g. piezoelectric-type transducers, owing to the inverse piezoelectric effect, transform the electric oscillations into elastic ultrasonic oscillations of a fluid with which they come in contact.

The first emitting transducer 24 is mounted directly on the wall of the vessel 49 containing the fluid 1 under study and forms in the wall material longitudinal ultrasonic oscillations 2 which are radiated into the slurry 1 under study.

The wavelength of the ultrasonic oscillations 2 emitted by the emitting ultrasonic transducer 24 is chosen to be of the same order (commensurate with) as the particle size of solid phase of the fluid 1 under study. It should be noted that frequency of the ultrasonic oscillations thus formed should be such (high enough) that there should be no gas bubbles of resonance size for such frequency. In this case the amount of damping of the ultrasonic oscillations 2 that passed through the fluid 1 under study is substantially determined only by the size of solid phase particles and their concentration.

For evaluation of concentration of solid phase, the amount of damping of the Lamb waves 3 that pass through a predetermined distance 1 along the wall of the vessel 49 containing the fluid 1 under study is measured. For forming the Lamb waves 3, the emitting ultrasonic transducer 35 is mounted on the forming prism 36 which is secured to the wall of the vessel 49 containing the fluid 1 under study.

The angle at which the ultrasonic oscillations 2 are directed into the wall of the vessel 49 containing the fluid 1 under study through the forming prism 36 is chosen in such a manner as to generate the Lamb waves 3 in the wall.

When the Lamb waves 3 propagate through the wall of the vessel 49 containing the fluid 1 under study, the amount of their damping is only determined by concentration of solid phase of slurries.

The receiving ultrasonic transducer 25, owing to the direct piezoelectric effect, transforms the ultrasonic oscillations 2 that passed through the fluid 1 under study into electric oscillations. The same process occurs in the receiving ultrasonic transducer 37 for the Lamb waves 3 that pass through a predetermined distance along the wall of the vessel 49 containing the fluid 1 under study.

The received pulses are amplified in the amplifiers 26, 39 and are fed to the electronic switches 27, 40.

Pulses formed by the multivibrator 46 trigger the one-shot delay multivibrators 29, 42 which generate square pulses, e.g. positive pulses, the length of which is equal to the minimum time during which the ultrasonic oscillations 2 propagate through the fluid 1 under study and minimum time during which the Lamb waves 3 pass through a predetermined distance I along the wall of the vessel 49 containing the fluid 1 under study, respectively. The differentiators 30, 43 differentiate the positive square pulses formed by the one-shot delay multivibrators 29, 42, these pulses being transformed into two successive short positive and negative pulses. The amplitude limiters 31, 44 let through only the second, negative pulse which will trigger the one-shot forming multivibrators 32, 45. The length of pulses formed by the forming one-shot multivibrators 32, 45 is chosen in such a manner that it should correspond to the informative part of the pulses of the ultrasonic oscillations 2 that passed through the fluid 1 under study and Lamb waves 3 that passed through a predetermined distance I along the wall of the vessel 49 containing the fluid 1 under study.

The pulses formed by the forming one-shot multivibrators 45 gate open the electronic switches 27, 40 which will pass through only the informative part of pulses of the ultrasonic oscillations 2 that pass through the fluid under study and the Lamb waves 3 that pass through a predetermined distance I along the wall of the vessel 49 containing the fluid 1 under study.

The amplitude of the Lamb waves 3 that pass through a predetermined distance I along the wall of the vessel 49 containing the fluid 1 under study will characterize concentration of solid phase of a slurry.

The logarithmic converters 28, 41 compute logarithms of amplitudes of the signals that pass through the electronic switches 27, 40.

The subtraction unit 47 computes the difference between logarithms of the measured amplitudes, and the division unit computes the value of S.

Figure 4:
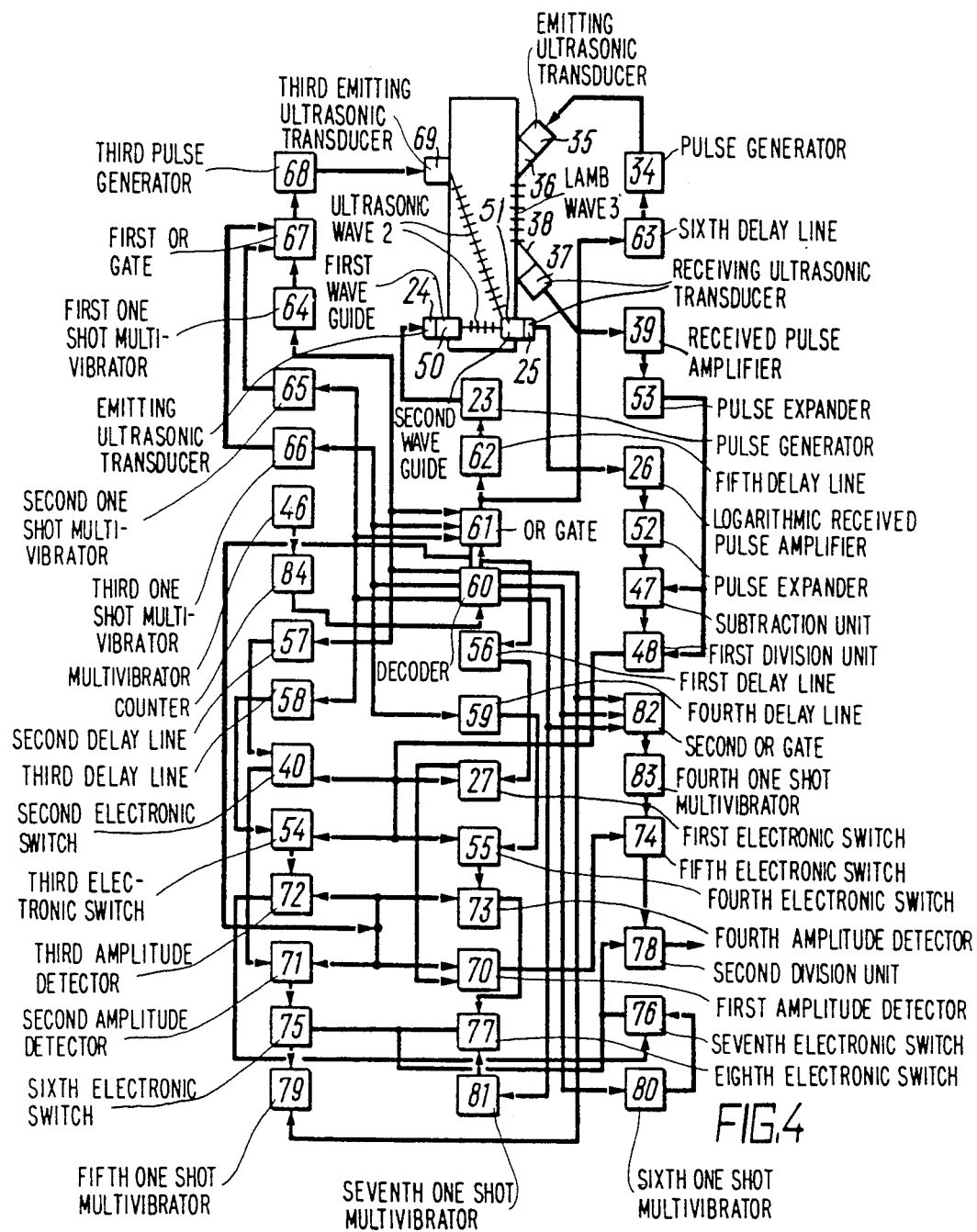
FIG. 4 shows a block-diagram of an apparatus for carrying out the method for measuring parameters of solid phase of slurries which is designed for measuring concentration of solid phase, concentration of a critical particle size fraction of solid phase and concentration of a useful component in the critical particle size fractions of the fluid under study, according to the invention.

An apparatus for carrying out the method for measuring parameters of solid phase of slurries, which allows concentration of solid phase, concentration of a critical particle size fraction and concentration of a useful component in critical particle size fractions of a fluid under study to be measured also comprises two measurement channels (FIG. 4).

The first measurement channel consists of a series circuit including a pulse generator 23, an emitting ultrasonic transducer 24 mounted on a wave guide 50, a receiving ultrasonic transducer 25 mounted on a wave guide 51, a received pulse amplifier 26, and a pulse expander 52.

The second measurement channel consists of a series circuit including a pulse generator 34, an emitting ultrasonic transducer 35 mounted on a forming prism 36, a receiving ultrasonic transducer 37 mounted on a forming prism 38, a received pulse amplifier 39, and a pulse expander 53. The received pulse amplifiers 26 and 39 of the first and second measurement channels comprise logarithmic amplifiers.

To the outputs of the pulse expanders 52, 53 of both measurement channels are connected inputs of a subtraction unit 47 having its output connected to one of the inputs of a division unit having its second input connected to the output of the pulse expander 53 of the second measurement channel.

The output of a first division unit 48 is connected to the second inputs of first 27, second 40, third 54 and fourth 55 electronic switches each having its first input connected, via a first 56, second 57, third 58 and fourth 59 delay lines, to the first four outputs of a decoder 60 which are also connected to the inputs of an OR gate 61 having its output which is connected, via a fifth 62 and a sixth 63 delay lines, to the inputs of the pulse generators 23, 34 of both measurement channels.

To the second, third and fourth outputs of the decoder 60 are connected first 64, second 65 and third 66 one-shot multivibrators having their outputs connected to the inputs of a first OR gate 67 having its output which is connected, via a third generator 68, to a third emitting ultrasonic transducer 69.

To the outputs of the first 27, second 40, third 54 and fourth 55 electronic switches are connected the first inputs of a first, 70, second 71, third 72 and fourth 73 amplitude detector having their second inputs connected to the eight output of the decoder 60 and the outputs connected to the first inputs of fifth 74, sixth 75, seventh 76 and eighth 77 electronic switches.

To the output of the fifth electronic switch 74 is connected the first input of a second division unit 78 having its second input connected to the outputs of the sixth 75, seventh 76 and eighth 77 electronic switches having their second inputs connected, via a fifth 79, sixth 80 and seventh 81 one-shot multivibrators, to the fifth, sixth and seventh outputs of the decoder 60 and to the inputs of a second OR gate 82 having its output connected, via a fourth one-shot multivibrator 83, to the second input of the fifth electronic switch 74.

To the input of the decoder 60 is connected a counter 84 which is connected to the one-shot multivibrator 46.

The third emitting ultrasonic transducer 69 is mounted in the top part of the vessel 49 containing the fluid 1 under study, in the bottom part of which there are provided wave guides 50, 51 supporting the emitting 24 and receiving 25 ultrasonic transducers of the first measurement channel and also the forming prisms 36, 38 supporting the emitting 35 and receiving 38 ultrasonic transducers of the second measurement channel.

The forming prisms 36, 38 may also be mounted on a measurement plate covering a longitudinal aperture in the wall of the vessel 49 containing the fluid 1 under study.

The apparatus for measuring parameters of solid phase of slurries shown in FIG. 4 functions in the following manner.

The multivibrator 46 generates square pulses which go to an electronic pulse distributor built around the counter 84 and decoder 60 having eight outputs. Thus one control cycle consists of eight steps. At the first step, a pulse from the first output of the decoder 60 will pass through the OR gate 61, fifth 62 and sixth 63 delay lines to trigger the first 23 and second 34 pulse generators. To reduce interference between the measurement channels, the pulse delay time in the delay lines 62, 63 is chosen in such a manner as to ensure a time shift between the periods of starting the first 23 and second 34 pulse generators which, when triggered, will generate trains of high-frequency electric oscillations at a predetermined frequency and pulse length.

The emitting ultrasonic transducers 24, 35, e.g. of the piezoelectric type, transform the electric signal into elastic oscillations of a medium with which they come in contact.

The first emitting ultrasonic transducer 24 emits, through the first wave guide 50, ultrasonic oscillations 2 into the fluid 1 under study in the vessel 49 in the direction toward the first receiving ultrasonic transducer 25 mounted on the second wave guide 51. The second emitting ultrasonic transducer 35 forms, through the first forming prism 36, in the wall of the vessel 49 (or measurement plate) the Lamb waves 3 which, having passed through the second forming prism 38, are received by the second receiving ultrasonic transducer 37.

The amount of damping of the high-frequency ultrasonic oscillations 2 when they pass from the first emitting ultrasonic transducer 24 toward the first receiving ultrasonic transducer 25 substantially depends only on particle size of solid phase and their concentration.

When the Lamb waves 3 pass through a predetermined distance l along the wall of the vessel 49 containing the fluid 1 under study, the amount of their damping only depends on concentration of solid phase of slurries.

The ultrasonic (elastic) oscillations 2 that pass through the fluid 1 under study and the Lamb waves that pass through a predetermined distance along the wall of the vessel 49 containing the fluid 1 under study are transformed into electric oscillations by the receiving ultrasonic transducers 25, 37.

The high-frequency electric oscillations are amplified on logarithmic scale and detected in logarithmic amplifiers 26, 39. As the length of the formed pulses is short, it is expanders 52, 53 without changes in the amplitude.

The difference between logarithms of the received signals is determined in the subtraction unit 47, and the first division unit 48 computes the value of S.

The amplitude of the Lamb waves 3 that pass through a predetermined distance 1 along the wall of the vessel 49 containing the fluid 1 under study will characterize concentration of solid phase of the fluid 1 under study and the value of S is the concentration of a critical particle size fraction of the slurry 1 under study.

A pulse from the first output of the decoder 60 will pass through the first delay line 56 to gate open the first electronic switch 27. Its delay time in the first delay line 56 is determined by the time of propagation of the ultrasonic oscillations in the fluid 1 under study and the Lamb waves 3 in the wall of the vessel 49 containing the fluid 1 under study, and this delay time is chosen in such a manner as to gate open the first electronic switch 27 by the moment the value of S is computed in the division unit 48.

The first amplitude detector 70 will hold ("store") the value of $S_o$.

The second, third and fourth control steps are effected similarly to the first step since the second, third and fourth pulses from the second, third and fourth outputs, respectively, of the decoder 60 will also trigger the pulse generators 23, 34 via the OR gate 61.

At the same time, each of these pulses will trigger the first 64, second 65 and third 66 one-shot multivibrators which, via the OR gate 67, will trigger the third generator 68 forming powerful electric oscillations which are transformed by the third emitting ultrasonic transducer 69 into elastic oscillations of fluid.

Acoustic currents and radiation pressure of the sonic radiation 10 are generated under the action of the powerful ultrasonic oscillations 2 thus formed to cause displacements of solid phase particles in the fluid 1 under study away from the third emitting ultrasonic transducer 69 in the direction toward the wall of the vessel 49 on which are mounted the forming prisms 36, 38 of the second measurement channel.

The displacement of solid phase particles will cause a change in their distribution by size and concentration in the zone adjacent to the wall of the vessel 49 on which are mounted the forming prisms 36, 38 of the second measurement channel and also in the zone between the wave guides 50, 51 of the first measurement channel.

The amount of redistribution of these parameters for particles of identical size located at a predetermined distance from the third emitting ultrasonic transducer 69 depends only on specific gravity of the particle material.

In practice, the material of the particles is in the form of a combination of several components one of which is a useful component the concentration of which should be measured.

Since the specific gravity of the useful component is known, the amount of displacement of particles of a known size consisting of this component only under the action of acoustic currents and radiation pressure of the sonic radiation 10 of a known intensity is determined analytically or by way of experiments.

The intensity of action of these factors will change upon a change of either amplitude or length when powerful ultrasonic oscillations formed by the third emitting ultrasonic transducer 69 are applied.

In case of the pulsed nature of action of powerful ultrasonic oscillations at a fixed amplitude the effect of the acoustic currents and radiation pressure of the sonic radiation 10 formed thereby upon a particle of solid phase of a slurry depends on the pulse length.

The length of pulses formed by the first 64, second 65 and third 66 one-shot multivibrators is chosen in such a manner that the effect of the acoustic currents and radiation pressure of the sonic radiation 10 be sufficient to cause a displacement of particles of three, and generally, more than three critical particle size fractions of solid phase of slurries.

The computed value of S for each case ($S^I$, $S^{II}$, $S^{III}$) is fed, via the second 40, third 54 and fourth 55 electronic switches gated open by pulses fed from the second, third and fourth outputs of the decoder 60 and delayed in the delay lines 57, 58, 59, to the second, third and fourth amplitude detectors 71, 72, 73 which will hold the amplitudes. The delay time in the delay lines 57, 58, 59 is chosen bearing in mind the same considerations as those for the delay line 56.

Pulses fed from the fifth, sixth and seventh outputs of the decoder 60 will gate open, via the fifth, sixth and seventh one-shot multivibrators 79, 80, 81, the sixth, seventh and eighth electronic switches 75, 76, 77.

Each of the pulses going from the fifth, sixth and seventh outputs of the decoder 60 will gate open, via the second OR gate 82 and the fourth one-shot multivibrator 83, the fifth electronic switch 74. The values of $S_o$ and $S^I$, $S_o$ and $S^{II}$, $S_o$ and $S^{III}$ are fed in pairs to the second division unit where concentration r of the useful component is computed:

$$r = \frac{S^{(i)}}{S_o}, i = 1, 2, 3$$

Figure 5:
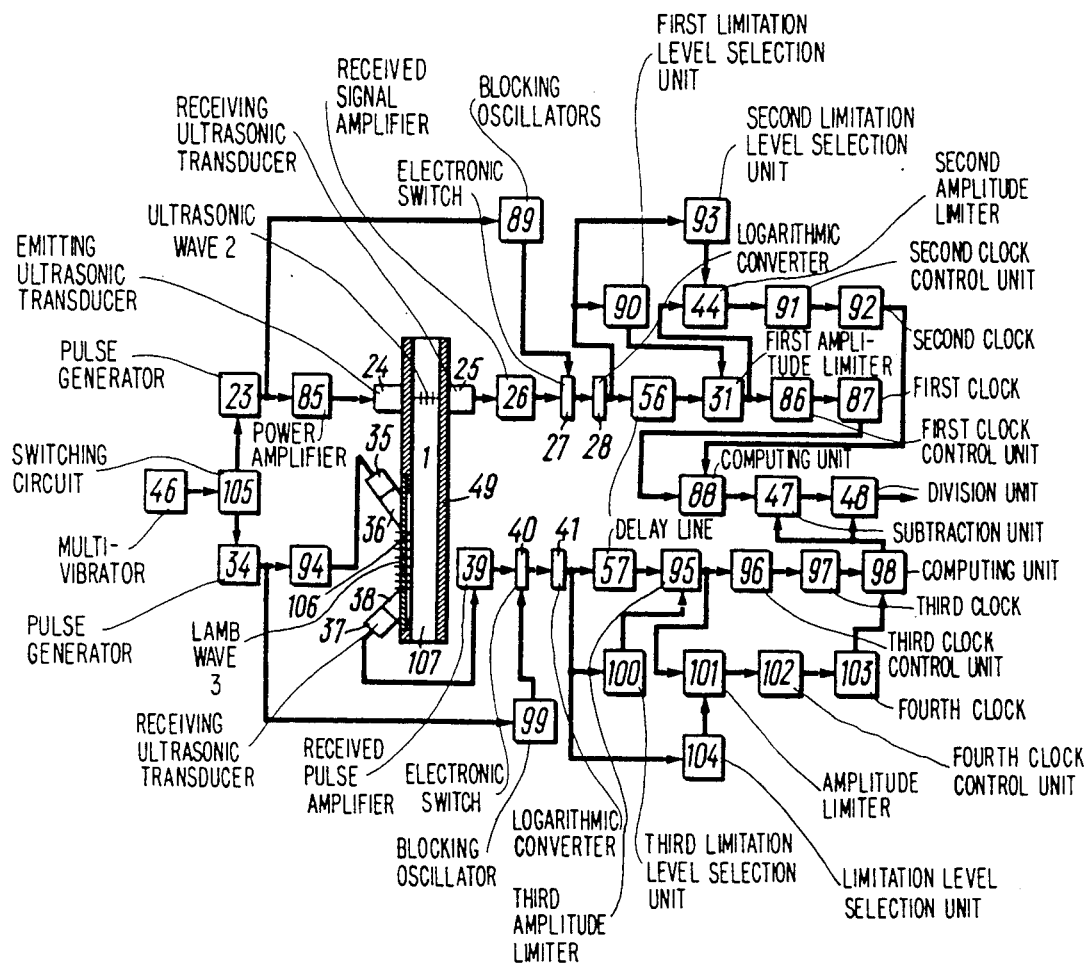
FIG. 5 shows a block-diagram of an apparatus for carrying out the method for measuring parameters of solid phase of slurries which is designed for measuring concentration of solid phase and concentration of a critical particle size fraction of solid phase with the control of the length of received pulses of ultrasonic oscillations that passed through the fluid under study and Lamb waves that passed through a predetermined distance along the wall of a vessel containing the fluid under study, according to the invention.

Still another embodiment of the apparatus for measuring parameters of solid phase of slurries is shown in FIG. 5 and also comprises two measurement channels.

The first channel comprises a series circuit including a pulse generator 23, a power amplifier 85, and an emitting ultrasonic transducer 24 and also a series circuit including a receiving ultrasonic transducer 25, a received signal amplifier 26, an electronic switch 27, a logarithmic converter 28, a delay line 56, a first amplitude limiter 31, a first circuit 86 for controlling a clock 87, and a unit 88 for computing the difference between lengths of pulses at different limitation levels.

A blocking oscillator 89 is connected between the pulse generator 23 and electronic switch 27 and a unit 90 for selecting limitation level is connected between the logarithmic converter 28 and the limiter 31.

To the output of the amplitude limiter 31 are connected a second amplitude limiter 44, a second circuit for controlling a clock 92 and the clock 92 forming a series circuit, the output of the clock being connected to the second input of the computing unit 88. Between the logarithmic converter 28 and the second amplitude limiter 44 is connected a second unit 93 for selecting limitation level.

The second measurement channel comprises a series circuit including a pulse generator 34, a power amplifier 94, an emitting ultrasonic transducer 35, a receiving ultrasonic transducer 37, a received pulse amplifier 39, an electronic switch 40, a logarithmic converter 41, a delay line 57, a third amplitude limiter 95, a third circuit 95 for controlling a clock 97, the third clock 97 and a unit 98 for computing the difference between pulse lengths at different limitation levels.

A blocking oscillator 99 is provided between the pulse generator 34 and electronic switch 40. A third unit 100 for selecting limitation level is provided between the logarithmic converter 41 and third amplitude limiter 95. A series circuit including a fourth amplitude limiter 101, a fourth circuit for controlling a clock 103 and the fourth clock 103 is provided between the third amplitude limiter 95 and the subtraction unit 98.

A fourth unit 104 for selecting limitation level is provided between the logarithmic converter 41 and fourth amplitude limiter 101. A subtraction unit 47, having an output connected to one input of the division unit 48 having its second input connected to the output of the unit 98 for computing the difference between the pulse lengths at different limitation levels, is provided between the units 88 and 98 for computing the difference between pulse lengths at different limitation levels. A switching circuit 105 having an input to which is connected a multivibrator 46 is connected between the pulse generators 23 and 34. The emitting ultrasonic transducer 35 is mounted on a forming prism 36, and the receiving ultrasonic transducer 37 is mounted on a forming prism 38. A measurement plate 106 covers a longitudinal aperture 107 in the wall of a measurement vessel 49.

The apparatus functions in the following manner.

The pulse generators 23, 34 form square pulses filled with sinusoidal oscillations. The frequency of oscillations formed by the pulse generator 23 in the first measurement channel I is chosen in such a manner that the wavelength of these oscillations be commensurate with particle size of solid phase in the fluid 1 under study.

The sinusoidal electric oscillations amplified in the power amplifiers 85, 94 are transformed into ultrasonic elastic oscillations of the medium and are emitted by the emitting ultrasonic transducer 24 into the fluid 1 under study and by the emitting ultrasonic transducer 35, via the forming prism 36, into the walls of the vessel 49 or into the measurement plate 106 covering the longitudinal aperture 107 of the measurement vessel 49 containing the fluid 1 under study, in which the Lamb waves 3 are induced.

The blocking oscillators 89, 99 are triggered by the leading edge of square pulses generated by the pulse generators 23, 34, and pulses formed thereby will gate open the electronic switches 27, 40 which will let through, during a selected time interval, signals from the received signal amplifiers 26, 39.

The logarithmic converters 28, 41 form pulses having amplitudes proportional to the logarithm of the amplitude of the pulses that passed through the electronic switches 27, 40.

The received pulses go, via the delay lines 56, 57, to the variable amplitude limiters 31, 95. The pulse arrival delay time depends on characteristics of the units 90 and 100 for selecting limitation level which will form limitation level in accordance with the current value of amplitude of the received pulse and pre-set values of ratios of the amplitude of the received pulse to the limitation level. Therefore, the absolute value of limitation level will change proportionally with the amplitude of the received pulse, the ratio of this level to the pulse amplitude remaining unchanged. This facility makes it possible to avoid the influence of fluctuations of damping of the ultrasonic oscillations 2 caused by various factors when they pass through the fluid 1 and the influence of fluctuations of damping of the Lamb waves 3 that pass through a predetermined distance I along the wall of the vessel 49 containing the fluid 1 under study on the length of the received pulse at the formed measurement levels.

The variable amplitude limiters 44, 101, in combination with the units 93, 104 for selecting limitation levels, will form a second level of limitation of the received pulse. The clock control circuits 86, 91, 96, 102 will trigger the clocks 87, 92, 97, 102 by the moment the limitation of the amplitude of the received pulses is started and will disable them when the amplitude of these pulses will start decreasing.

The first unit 88 for computing the difference between the pulse lengths at different limitation levels will compute the difference α between lengths of a pulse of the ultrasonic oscillations 2 that passed through the fluid 1 under study at the formed measurement levels, and the second unit 98 for computing the difference between lengths of pulses at different limitation levels will compute the difference β of lengths of pulses of the Lamb waves 3 that passed along the wall of the vessel 49 containing the fluid under study. The difference α−β is computed in the subtraction unit 47.

The division unit 48 will compute the vale of $S_o$ which characterizes concentration of a critical particle size fraction of solid phase of a slurry:

$$S_o = \frac{\alpha - \beta}{\beta}.$$

The value of $S_o$ is transformed into a signal of a standard form and value in a scaling unit 104.

Therefore, the method and apparatus for measuring parameters of solid phase of slurries according to the invention make it possible to measure by a non-contact method concentration of solid phase, concentration of a critical particle size fraction of solid phase and concentration of a useful component in critical particle size fractions in a slurry under study without preliminary removal of the gaseous phase from the slurry using mechanical means. All this contributes to an improvement of accuracy and reliability of measurements and also to a reduction of the cost of equipment for measuring parameters of solid phase of slurries and operation cost of such equipment.

The method and apparatus for measuring parameters of solid phase of slurries according to the invention may be advantageously used in the mining and ore processing industry, chemical construction and neighbouring industries for measuring concentration, size and mineral.

We claim:

1. A method for measuring parameters of solid phase slurries, comprising:
    forming ultrasonic oscillation pulses;
    passing the ultrasonic oscillation pulses through a fluid under study containing the slurry, said fluid and slurry being contained in a vessel;
    measuring a first amplitude of the pulses of the ultrasonic oscillations that pass through the fluid;
    using the value of the amplitude to assess the concentration of the solid phase of the fluid;
    forming Lamb waves;
    passing the Lamb waves along a wall of the vessel containing the fluid;
    measuring a second amplitude of the Lamb waves that pass through a predetermined distance along the wall of the vessel containing the fluid, the value of this amplitude characterizing the concentration of the solid phase of the slurries;
    computing the difference between first and second logarithms of the first and second amplitudes of the ultrasonic oscillations that pass through the fluid and of the Lamb waves that pass through a predetermined distance along the wall of the vessel containing the fluid; and computing the ratio of said difference to said first logarithm which corresponds to the concentration of a critical particle size fraction of the solid phase of the slurries.

2. A method according to claim 1, further comprising the steps of:
    generating acoustic currents and radiation pressure of a sonic radiation of the fluid the radiation pressure having an intensity proportional to a mass of particles of the solid phase of slurries;
    subsequently determining, for several predetermined values of intensity of acoustic currents and radiation pressure of said sonic radiation, a quotient of division of computed ratios for several fixed values of intensity of acoustic currents and radiation pressure of said sonic radiation to the same value to characterize concentration of a useful component in critical particle size fractions of the slurry.

3. A method according to claim 1, further comprising the steps of:
    forming a first level of measurement of pulse lengths of the ultrasonic oscillations that pass through the fluid and forming a second level of measurement of Lamb waves that pass through a predetermined distance along the wall of the vessel containing the fluid which are consecutively amplitude-limited, the levels of measurement of these pulse lengths being varied proportionally with their amplitude;

measuring the length of the received pulses at the formed levels;

determining a difference between the measured values of the Lamb waves that pass through a predetermined distance along the wall of the vessel containing the fluid to characterize concentration of solid phase of slurries; and determining a ratio of the difference between the measured values for the ultrasonic oscillations that pass through the fluid to the difference between measured values for the Lamb waves that pass through a predetermined distance along the wall of the vessel containing the fluid, said ratio being the concentration of a critical particle size fraction of solid phase of slurries.

4. An apparatus for measuring parameters of solid phase slurries in a fluid under study, comprising:

a vessel having walls and containing the fluid;

a first wave amplitude measurement channel for generating ultrasonic waves through the fluid, comprising: a series circuit including a pulse generator, an emitting ultrasonic transducer mounted on one of the walls of the vessel, a receiving ultrasonic transducer mounted opposite the emitting ultrasonic transducer on one of the walls of the vessel, and a received signal amplifier; and a logarithmic converter having an input connected to an output of the received signal amplifier and an output;

a second wave amplitude measurement channel for forming Lamb waves in one of the walls of the vessel, comprising: a series circuit including a pulse generator, an emitting ultrasonic transducer, a receiving ultrasonic transducer, and a received signal amplifier; and a logarithmic converter having an input connected to an output of the received signal amplifier and an output, the emitting ultrasonic transducer and the receiving ultrasonic transducer being mounted to one of the walls of the vessel through forming prisms for forming Lamb waves in one of the walls of the vessel;

a subtraction unit having an output and inputs connected to the output of the logarithmic converter of the first wave amplitude measurement channel and the output of the logarithmic converter of the second wave amplitude measurement channel; and a first division unit having inputs connected to the output of the subtraction unit and the output of the logarithmic converter of the second wave amplitude measurement channel.

5. An apparatus according to claim 4, wherein the forming prisms are mounted on a plate which covers a longitudinal aperture of one of the walls of the vessel, and the plate is secured to one of the walls of the vessel.

6. An apparatus according to claim 4, wherein the first channel and the second channel each further comprises an additional series circuit, including a delay line, an amplitude limiter, a control circuit, and means for computing a difference between pulse lengths at different measurement levels of amplitude limitation, an input of each additional series circuit being connected to the respective output of the logarithmic converter, and an output of each additional series circuit being connected to the input of the subtraction unit.

7. An apparatus according to claim 6, wherein the first channel and the second channel each further comprises means for selecting amplitude limitation measurement level, connected in series after the respective logarithmic converter.

8. An apparatus according to claim 4, wherein the first channel and the second channel each further comprises a pulse expander having an input connected to the output of the respective received signal amplifier, an output of each respective pulse expander being connected to the subtraction unit, and the output of the pulse expander of the second channel being connected to the input of the division unit.

9. An apparatus according to claim 5, wherein the first channel and the second channel each further comprises a pulse expander having an input connected to the output of the respective received signal amplifier, an output of each respective pulse expander being connected to the subtraction unit, and the output of the pulse expander of the second channel being connected to the input of the division unit.

10. An apparatus according to claim 4, further comprising:

a counter having an input connected to the output of the received signal amplifier of the first channel and the output of the received signal amplifier of the second channel;

a first OR gate having a first output connected through a first delay line to the input of the pulse generator of the first channel, and a second output connected through a second delay line to the input of the pulse generator of the second channel;

a decoder having inputs connected to an output of the counter, and an output connected to an input of the first OR gate; and means for controlling measurement and computation of parameters of solid phase.

11. An apparatus according to claim 5, further comprising:

a counter having an input connected to the output of the received signal amplifier of the first channel and the output of the received signal amplifier of the second channel;

a first OR gate having a first output connected through a first delay line to the input of the pulse generator of the first channel, and a second output connected through a second delay line to the input of the pulse generator of the second channel;

a decoder having inputs connected to an output of the counter, and an output connected to an input of the first OR gate; and means for controlling measurement and computation of parameters of solid phase.

12. An apparatus according to claim 8, further comprising:

a counter having an input connected to the output of the received signal amplifier of the first channel and the output of the received signal amplifier of the second channel;

a first OR gate having a first output connected through a first delay line to the input of the pulse generator of the first channel, and a second output connected through a second delay line to the input of the pulse generator of the second channel;

a decoder having inputs connected to an output of the counter, and an output connected to an input of the first OR gate; and means for controlling measurement and computation of parameters of solid phase.

13. An apparatus according to claim 9, further comprising:
- a counter having an input connected to the output of the received signal amplifier of the first channel and the output of the received signal amplifier of the second channel;
- a first OR gate having a first output connected through a first delay line to the input of the pulse generator of the first channel, and a second output connected through a second delay line to the input of the pulse generator of the second channel;
- a decoder having inputs connected to an output of the counter, and an output connected to an input of the first OR gate; and
- means for controlling measurement and computation of parameters of solid phase.

14. An apparatus according to claim 12, wherein the means for controlling measurement and computation of parameters of solid phase comprises a series circuit including:
- a second OR gate having inputs;
- a pulse generator; and
- an emitting transducer secured to one of the walls of the vessel above the emitting transducer of the first channel and above the emitting transducer of the second channel, and opposite to the emitting transducer and receiving transducer of the second channel, the inputs of the second OR gate being connected through respective one-shot multivibrators to the inputs of the first OR gate and to outputs of the decoder.

15. An apparatus according to claim 13, wherein the means for controlling measurement and computation of parameters of solid phase comprises a series circuit including:
- a second OR gate having inputs;
- a pulse generator; and
- an emitting transducer secured to one of the walls of the vessel above the emitting transducer of the first channel and above the emitting transducer of the second channel, and opposite to the emitting transducer and receiving transducer of the second channel, the inputs of the second OR gate being connected through respective one-shot multivibrators to the inputs of the first OR gate and to outputs of the decoder.

16. An apparatus according to claim 10, wherein the means for controlling measurement and computation of parameters of solid phase comprises a second division unit having inputs and an output, and at least four identical series circuits each including:
- a delay line having an input;
- a first electronic switch having a data input;
- an amplitude detector having a control input; and
- a second electronic switch having a control input;
- outputs of at least three of the identical circuits being joined, the input of each respective delay line being connected to inputs of the decoder, the data input of each respective first electronic switch being connected to a control input of the first division unit, the control input of the second electronic switch of a remaining identical series circuit being connected through a series connected second OR gate and a first one-shot multivibrator to one output of the decoder, the control input of the second electronic switch of the at least three of the identical series circuits being connected through respective second one-shot multivibrators to outputs of the decoder, the control input of each respective amplitude detector being connected to outputs of the decoder, outputs of the four identical series circuits being connected to the inputs of the second division unit, and the output of the second division unit being a data output of the apparatus.

17. An apparatus according to claim 11, wherein the means for controlling measurement and computation of parameters of solid phase comprises a second division unit having inputs and an output, and at least four identical series circuits each including:
- a delay line having an input;
- a first electronic switch having a data input;
- an amplitude detector having a control input; and
- a second electronic switch having a control input;
- outputs of at least three of the identical circuits being joined, the input of each respective delay line being connected to inputs of the decoder, the data input of each respective first electronic switch being connected to a control input of the first division unit, the control input of the second electronic switch of a remaining identical series circuit being connected through a series connected second OR gate and a first one-shot multivibrator to one output of the decoder, the control input of the second electronic switch of the at least three of the identical series circuits being connected through respective second one-shot multivibrators to outputs of the decoder, the control input of each respective amplitude detector being connected to outputs of the decoder, outputs of the four identical series circuits being connected to the inputs of the second division unit, and the output of the second division unit being a data output of the apparatus.

18. An apparatus according to claim 12, wherein the means for controlling measurement and computation of parameters of solid phase comprises a second division unit having inputs and an output, and at least four identical series circuits each including:
- a delay line having an input;
- a first electronic switch having a data input;
- an amplitude detector having a control input; and
- a second electronic switch having a control input;
- outputs of at least three of the identical circuits being joined, the input of each respective delay line being connected to inputs of the decoder, the data input of each respective first electronic switch being connected to a control input of the first division unit, the control input of the second electronic switch of a remaining identical series circuit being connected through a series connected second OR gate and a first one-shot multivibrator to one output of the decoder, the control input of the second electronic switch of the at least three of the identical series circuits being connected through respective second one-shot multivibrators to outputs of the decoder, the control input of each respective amplitude detector being connected to outputs of the decoder, outputs of the four identical series circuits being connected to the inputs of the second division unit, and the output of the second division unit being a data output of the apparatus.

19. An apparatus according to claim 13, wherein the means for controlling measurement and computation of parameters of solid phase comprises a second division unit having inputs and an output, and at least four identical series circuits each including:
 a delay line having an input;
 a first electronic switch having a data input;
 an amplitude detector having a control input; and
 a second electronic switch having a control input;
 outputs of at least three of the identical circuits being joined, the input of each respective delay line being connected to inputs of the decoder, the data input of each respective first electronic switch being connected to a control input of the first division unit, the control input of the second electronic switch of a remaining identical series circuit being connected through a series connected second OR gate and a first one-shot multivibrator to one output of the decoder, the control input of the second electronic switch of the at least three of the identical series circuits being connected through respective second one-shot multivibrators to outputs of the decoder, the control input of each respective amplitude detector being connected to outputs of the decoder, outputs of the four identical series circuits being connected to the inputs of the second division unit, and the output of the second division unit being a data output of the apparatus.

20. An apparatus according to claim 16, further comprising two identical means for forming limitation level, each comprising:
 a unit for selecting limitation level, having an input connected to the output of the respective logarithmic converter of the first channel and the second channel, and an output;
 a first amplitude limiter having an input connected to the output of the unit for selecting limitation level;
 a series circuit including a second amplitude limiter and a timer control circuit, having an output connected to an input of a unit for computing difference between pulse lengths, and an input connected to the respective first amplitude limiter.

21. An apparatus according to claim 17, further comprising two identical means for forming limitation level, each comprising:
 a unit for selecting limitation level, having an input connected to the output of the respective logarithmic converter of the first channel and the second channel, and an output;
 a first amplitude limiter having an input connected to the output of the unit for selecting limitation level;
 a series circuit including a second amplitude limiter and a timer control circuit, having an output connected to an input of a unit for computing difference between pulse lengths, and an input connected to the respective first amplitude limiter.

22. An apparatus according to claim 18, further comprising two identical means for forming limitation level, each comprising:
 a unit for selecting limitation level, having an input connected to the output of the respective logarithmic converter of the first channel and the second channel, and an output;
 a first amplitude limiter having an input connected to the output of the unit for selecting limitation level;
 a series circuit including a second amplitude limiter and a timer control circuit, having an output connected to an input of a unit for computing difference between pulse lengths, and an input connected to the respective first amplitude limiter.

23. An apparatus according to claim 19, further comprising two identical means for forming limitation level, each comprising:
 a unit for selecting limitation level, having an input connected to the output of the respective logarithmic converter of the first channel and the second channel, and an output;
 a first amplitude limiter having an input connected to the output of the unit for selecting limitation level;
 a series circuit including a second amplitude limiter and a timer control circuit, having an output connected to an input of a unit for computing difference between pulse lengths, and an input connected to the respective first amplitude limiter.

* * * * *